United States Patent [19]

Cann et al.

[11] Patent Number: 4,861,846

[45] Date of Patent: Aug. 29, 1989

[54] PROCESS FOR SIMULTANEOUSLY DIMERIZING ETHYLENE AND COPOLYMERIZING ETHYLENE WITH THE DIMERIZED PRODUCT

[75] Inventors: Kevin J. Cann, Belle Mead; Michael W. Chen, Bridgewater; Frederick J. Karol, Belle Mead, all of N.J.

[73] Assignee: Union Carbidae Corporation, Danbury, Conn.

[21] Appl. No.: 714,828

[22] Filed: Mar. 22, 1985

[51] Int. Cl.$^4$ .......................... C08F 2/34; C08F 210/16
[52] U.S. Cl. ........................................ 526/75; 502/118; 526/119; 526/348.6; 526/901
[58] Field of Search ................. 526/119, 75; 585/512, 585/513

[56] References Cited

U.S. PATENT DOCUMENTS

| | | | |
|---|---|---|---|
| 2,953,552 | 9/1960 | Stampa et al. | 526/119 |
| 3,526,616 | 1/1970 | Delbouille et al. | 526/125 |
| 3,564,071 | 2/1971 | Izawa et al. | 260/683.15 |
| 3,900,454 | 8/1975 | Sato et al. | 526/119 |
| 3,901,863 | 8/1975 | Berger et al. | 526/119 |
| 3,969,429 | 1/1976 | Belov et al. | 260/683.15 D |
| 4,133,944 | 1/1979 | Cooper et al. | 526/159 |
| 4,258,159 | 3/1981 | Bienfait | 526/119 |
| 4,329,255 | 5/1982 | Beach et al. | 526/119 |
| 4,343,755 | 8/1982 | Miller et al. | 526/125 |

OTHER PUBLICATIONS

David L. Beach and Yury V. Kissin, *Journal of Polymer Science: Polymer Chemistry Edition*, vol. 22, 3027–3042 (1984).

*Primary Examiner*—Edward J. Smith
*Attorney, Agent, or Firm*—John S. Piscitello

[57] ABSTRACT

A process for producing copolymers of ethylene and butene-1 wherein the butene-1 comonomer is generated in situ within the polymerization reactor by a separately catalyzed ethylene dimerization reaction.

60 Claims, No Drawings

PROCESS FOR SIMULTANEOUSLY DIMERIZING ETHYLENE AND COPOLYMERIZING ETHYLENE WITH THE DIMERIZED PRODUCT

FIELD OF THE INVENTION

This invention relates to a process for producing copolymers of ethylene and butene-1 wherein the butene-1 comonomer is generated in situ within the polymerization reactor by a separately catalyzed ethylene dimerization reaction.

BACKGROUND OF THE INVENTION

Recently a low cost fluidized bed process for producing ethylene polymers having a density of from 0.86 g/cm$^3$ to 0.96 g/cm$^3$ was introduced into the marketplace. This process, which met with immediate success and has now become the industry standard, comprises continuously copolymerizing ethylene with one or more higher alpha olefin monomers, usually butene, by means of a catalyst composition prepared by (1) forming a precursor composition from a magnesium compound, titanium compound and electron donor compound, (2) diluting said precursor composition with an inert carrier material, and (3) activating the precursor composition with an organoaluminum compound. Such process is more completely described in U.S. Pat. Nos. 4,302,565, 4,302,566 and 4,303,771, and European patent publication 0 120 503.

While this process has substantially reduced the cost of producing ethylene polymers, the cost still remains higher than desired because of the relatively high cost of the higher alpha olefin comonomer employed in the process vis-a-vis the cost of ethylene, particularly in those areas of the world where the disparity in price between such comonomer and ethylene is substantial. In view of this, it would be desirable to reduce the cost of producing such comonomer in order to further reduce the cost of the process and the polymers produced thereby.

One method suggested for producing higher alpha olefin comonomer comprises oligomerizing ethylene to higher alpha olefins, e.g., dimerizing ethylene to produce butene. Such dimerization has only infrequently been attempted in situ during the polymerization of ethylene, however, because of the difficulty of producing a compatible dimerization and polymerization system, i.e., one wherein the dimerization catalyst and polymerization catalyst operate under the same reaction conditions and do not interfere with each other chemically. Such in situ dimerization would be desirable, however, as a means of eliminating one of the comonomers employed, simplifying the polymerization process, and reducing the overall cost of the polymers produced.

One means of simultaneously dimerizing ethylene in situ and copolymerizing ethylene with the dimerized product has been suggested in U.S. Pat. No. 4,133,944. This method employs a transition metal catalyst, such as a Ziegler-type catalyst, together with a dimerization catalyst, such as a titanium alkoxide, and an alkylaluminum compound, for this purpose and requires temperatures of from 100° C. to 350° C. and pressures of from 300–1000 kgm/cm$^2$.

While U.S. Pat. No. 3,526,616 suggests that simultaneous in situ dimerization and copolymerization of ethylene can be effected by means of a similar catalyst under milder temperature and pressure conditions, this patent requires that the transition metal compound employed be reacted with a bivalent metal hydroxychloride support in order to effect dimerization under such conditions.

The simultaneous in situ dimerization and copolymerization of ethylene with similar catalysts under mild temperature and pressure conditions has also been taught by David L. Beach and Yury V. Kissin (Dual Functional Catalysis for Ethylene Polymerization to Branched Polyethylene. I. Evaluation of Catalytic Systems, *Journal of Polymer Science: Polymer Chemistry Edition*, Vol. 22, 3027–3042 (1984)). This reference further teaches that while solubilized titanium alkoxides produce fairly active dimerization catalysts, insolubilized compounds make ineffective catalysts. Thus, this system depends upon the presence of a solvent for its effectiveness, and suggests that such system is not effective in a gas phase fluid bed process.

SUMMARY OF THE INVENTION

In accordance with the present invention it has now been discovered that ethylene can be simultaneously dimerized to produce butene-1 and copolymerized with the dimerized product in a gas phase fluidized bed process by means of a catalyst system comprising (a) a titanium tetraalkoxide, (b) a supported magnesium-titanium-based composition, and (c) a trialkylaluminum compound. Such process eliminates the use of comonomers other than ethylene, simplifies the polymerization process, and reduces the overall cost of the polymers produced.

DESCRIPTION OF THE PREFERRED EMBODIMENT

Surprisingly, the simultaneous dimerization of ethylene and copolymerization of ethylene with the dimerized product has been found to proceed smoothly and efficiently under mild conditions of temperature and pressure in the absence of a solvent without mutual interference between the dimerization and polymerization catalysts employed in the process. As a result, polymerization activity remains high, and ethylene copolymer having excellent morphological properties required for successful operation in a fluidized bed is produced in high yield. One would not have expected such results in the absence of the various precautions followed by the prior art.

Although some cis and some trans butene-2, as well as other ethylene oligomers, are produced by the process, the dimerization reaction proceeds with high selectivity and results in the production of butene-1 at a selectivity in excess of 80 percent, usually in excess of 85 percent. Among the butene isomers produced by the process, butene-1 is produced at a selectivity in excess of 85 percent, usually in excess of 90 percent.

The titanium tetraalkoxide employed in the process serves as the dimerization catalyst for ethylene when activated with the trialkylaluminum compound. The titanium tetraalkoxides which can be employed include those having the formula

$$Ti(OR)_4$$

wherein each R is a hydrocarbon radical free from aliphatic unsaturation, which radicals may be the same or different. Generally each R radical contains from 1 to 12 carbon atoms, usually from 1 to 6 carbon atoms. Such radicals may be aromatic, or cyclic, branched or straight chain aliphatic, and may be substituted with any substituent which is nonreactive with all the components of the catalyst composition and all other active components of the reaction system. Illustrative of such radicals are methyl, ethyl, n-propyl, isopropyl, n-butyl, isobutyl, tert-butyl, n-hexyl, cyclohexyl, 2-ethylhexyl, n-octyl, n-decyl, phenyl, tolyl, xylyl, and the like.

The titanium tetraalkoxide compounds can be used individually or in combination thereof, and include compounds such as titanium tetramethoxide, titanium tetraethoxide, titanium tetra-n-propoxide, titanium tetraisopropoxide, titanium tetra-n-butoxide, titanium tetraisobutoxide, titanium tetra-tert-butoxide, titanium tetra-n-hexoxide, titanium tetracyclohexoxide, titanium tetra-2-ethylhexoxide, titanium tetra-n-octoxide, titanium tetra-n-decoxide, titanium tetraphenoxide, titanium tetratoloxide, and titanium tetraxyloxide. Titanium tetraisobutoxide is particularly preferred.

The magnesium-titanium-based composition employed in the process serves as the polymerization catalyst for ethylene when activated with the trialkylaluminum compound. Such composition is formed by dissolving at least one titanium compound and at least one magnesium compound in at least one electron donor compound at a temperature of from about 20° C. up to the boiling point of the electron donor compound. The titanium compound(s) can be added to the electron donor compound(s) before or after the addition of the magnesium compound(s), or concurrent therewith. The dissolution of the titanium compound(s) and the magnesium compound(s) can be facilitated by stirring, and in some instances by refluxing, these two compounds in the electron donor compound(s). After the titanium compound(s) and the magnesium compound(s) are dissolved, the resulting product may be isolated by crystallization or by precipitation with an aliphatic or aromatic hydrocarbon containing from 5 to 8 carbon atoms, such as hexane, isopentane or benzene. The crystallized or precipitated product may be recovered as fine, free-flowing particles having an average particle size of from about 10 microns to about 100 microns after drying at temperatures up to 60° C.

About 0.5 mol to about 56 mols, and preferably about 1 mol to about 10 mols, of the magnesium compound(s) are used per mol of the titanium compound(s) in preparing this product.

The titanium compound(s) employed in preparing the magnesium-titanium-based composition has the structure $Ti(OR')_a X_b$ 

wherein

R' is an aliphatic or aromatic hydrocarbon radical containing from 1 to 14 carbon atoms, or COR" where R" is an aliphatic or aromatic hydrocarbon radical containing from 1 to 14 carbon atoms, X is selected from the group consisting of Cl, Br, I, and mixtures thereof, a is 0, 1 or 2, b is 1 to 4 inclusive, and a+b=3 or 4.

Suitable titanium compounds include $TiCl_3$, $TiCl_4$, $Ti(OCH_3)Cl_3$, $Ti(OC_6H_5)Cl_3$, $Ti(OCOCH_3)Cl_3$ and $Ti(OCOC_6H_5)Cl_3$. $TiCl_3$ is preferred because catalysts containing this material show particularly high activity at the temperatures employed in the process of the present invention.

The magnesium compound(s) employed in preparing the magnesium-titanium-based composition has the structure $MgX_2$ 

wherein X is selected from the group consisting of Cl, Br, I, and mixtures thereof.

Suitable magnesium compounds include $MgCl_2$, $MgBr_2$ and $MgI_2$. Anhydrous $MgCl_2$ is particularly preferred.

The electron donor compound(s) employed in preparing the magnesium-titanium-based composition is an organic compound which is liquid at 25° C. and in which the titanium and magnesium compounds are soluble. The electron donor compounds are known as such, or as Lewis bases.

Suitable electron donor compounds include the alkyl esters of aliphatic and aromatic carboxylic acids, aliphatic ethers, cyclic ethers and aliphatic ketones. Among these electron donor compounds the preferable ones are alkyl esters of saturated aliphatic carboxylic acids containing from 1 to 4 carbon atoms; alkyl esters of aromatic carboxylic acids containing from 7 to 8 carbon atoms; aliphatic ethers containing from 2 to 8 carbon atoms, preferably from 4 to 5 carbon atoms; cyclic ethers containing from 4 to 5 carbon atoms, preferably mono- or di-ethers containing 4 carbon atoms; and aliphatic ketones containing from 3 to 6 carbon atoms, preferably from 3 to 4 carbon atoms. The most preferred of these electron donor compounds include methyl formate, ethyl acetate, butyl acetate, ethyl ether, tetrahydrofuran, dioxane, acetone and methyl ethyl ketone.

After the magnesium-titanium-based composition has been prepared it is diluted with an inert carrier material by (1) mechanically mixing or (2) impregnating such composition into the carrier material.

Mechanical mixing of the inert carrier and the magnesium-titanium-based composition is effected by blending these materials together using conventional techniques. The blended mixture suitably contains from about 3 percent by weight to about 50 percent by weight of the magnesium-titanium-based composition.

Impregnation of the inert carrier material with the magnesium-titanium-based composition may be accomplished by dissolving the magnesium-titanium-based composition in the electron donor compound, and then admixing the carrier with the dissolved composition. The solvent is then removed by drying at temperatures up to about 85° C.

The carrier may also be impregnated with the magnesium-titanium-based composition by adding the carrier to a solution of the chemical raw materials used to form said composition in the electron donor compound, without isolating said composition from said solution. The excess electron donor compound is then removed by drying at temperatures up to about 85° C. Suitably, the impregnated carrier material contains from about 3 percent by weight to about 50 percent by weight, preferably from about 10 percent by weight to about 30 percent by weight, of the magnesium-titanium-based composition.

When prepared as disclosed above the blended or impregnated magnesium-titanium-based composition has the formula $Mg_m Ti(OR')_n X_p [ED]_q$ 

wherein R' is an aliphatic or aromatic hydrocarbon radical containing from 1 to 14 carbon atoms, or COR" wherein R" is also an aliphatic or aromatic hydrocarbon radical containing from 1 to 14 carbon atoms, X is selected from the group consisting of Cl, Br, I, and mixtures thereof,
ED is an electron donor compound,
m is 0.5 to 56, preferably 1.5 to 5,
n is 0, 1 or 2,
p is 2 to 116, preferably 6 to 14, and
q is 2 to 85, preferably 3 to 10.

The carrier materials employed to dilute the magnesium-titanium-based composition are solid, particulate, porous materials which are nonreactive with all the other components of the catalyst composition and all other active components of the reaction system. These carrier materials include inorganic materials, such as oxides of silicon and/or aluminum, and phosphates of aluminum. The carrier materials are used in the form of dry powders having an average particle size of from about 10 microns to about 250 microns, preferably from about 20 microns to about 150 microns. These materials are also porous and have a surface area of at least 3 square meters per gram, and preferably at least 50 square meters per gram. Polymerization activity of the catalyst, i.e., productivity, can be improved by employing a silica support having an average pore size of at least 80 Angstrom units, preferably at least 100 Angstrom units. The carrier material should be dry, that is, free of absorbed water. Drying of the carrier material can be effected by heating, e.g., at a temperature of at least 600° C. when silica is employed as the support. Alternatively, when silica is employed, it may be dried at a temperature of at least 200° C. and treated with about 1 weight percent to about 8 weight percent of one or more of the organoaluminum activator compounds described below. Modification of the support with an aluminum compound in this manner provides the catalyst composition with increased activity and also improves particle morphology of the resulting ethylene copolymers. Other organometallic compounds, such as diethylzinc, may also be used to modify the support.

In order for the titanium tetraalkoxide to be useful as a dimerization catalyst, and for the magnesium-titanium-based composition to be useful as a polymerization catalyst, they must be activated with a compound capable of transforming the titanium atoms of these materials to a state which will effect the desired dimerization and polymerization reactions. Such activation is effected by means of a trialkylaluminum compound having the formula:

$$AlR_3'''$$

wherein each R''' is a saturated hydrocarbon radical containing from 1 to 14 carbon atoms, which radicals may be the same or different. Such radicals may be substituted with any substituent which is nonreactive with all the components of the catalyst composition and all other active components of the reaction system.

The activator compounds can be employed individually or in combination thereof, and include compounds such as $Al(C_2H_5)_3$, $Al(i-C_4H_9)_3$, $Al(C_6H_{13})_3$ and $Al(C_8H_{17})_3$. Triisobutylaluminum is particularly preferred because titanium tetraalkoxides activated with this material show particularly high dimerization activity.

If desired, the magnesium-titanium-based composition may be partially activated before it is introduced into the polymerization reactor. However, any activation undertaken outside of the polymerization reactor should be limited to the addition of an amount of activator compound which does not raise the molar ratio of activator compound:electron donor in the magnesium-titanium-based composition beyond 1.4:1. Preferably, when activation is effected outside the reactor in this manner, the activator compound is employed in an amount which will provide the magnesium-titanium-based composition with an activator compound:electron donor molar ratio of from about 0.1:1 to about 1.0:1. Such partial activation is carried out in a hydrocarbon solvent slurry followed by drying of the resulting mixture, to remove the solvent, at temperatures of from about 20° C. to about 80° C., preferably from about 50° C. to about 70° C. The resulting product is a free-flowing solid particulate material which can be readily fed to the polymerization reactor where activation is completed with additional activator compound.

Partial activation of the magnesium-titanium-based composition before it is introduced in the polymerization reactor may be effected by means of organoaluminum compounds having the formula $$Al(R''')_dX'_eH_f$$

wherein
X' is Cl or OR'''',
R''' and R'''' are saturated hydrocarbon radicals containing from 1 to 14 carbon atoms, which radicals may be the same or different, and, if desired, substituted with any substituent which is nonreactive with all the components of the catalyst composition and all other active components of the reaction system,
e is 0 to 1.5,
f is 0 or 1, and
d+e+f=3.

Such activator compounds can be employed individually or in combination thereof and include compounds such as $Al(C_2H_5)_3$, $Al(C_2H_5)_2Cl$, $Al_2(C_2H_5)_3Cl_3$, $Al(C_2H_5)_2H$, $Al(C_2H_5)_2(OC_2H_5)$, $Al(i-C_4H_9)_3$, $Al(i-C_4H_9)_2H$, $Al(C_6H_{13})_3$ and $Al(C_8H_{17})_3$.

Alternatively, when the magnesium-titanium-based composition is impregnated in the inert carrier, it may, if desired, be completely activated in the polymerization reactor without any prior activation outside of the reactor, in the manner described in U.S Pat. No. 4,383,095, the disclosure of which is incorporated herein by reference.

The titanium tetraalkoxide, the partially activated or totally unactivated magnesium-titanium-based composition, and the required amount of activator compound necessary to complete activation of both titanium materials are usually introduced into the reactor through separate feed lines in order to more effectively control the amount of each of these materials in the reactor. However, if desired, any two or all three materials can be added together. If desired, the titanium tetraalkoxide may even be impregnated upon the same inert carrier as the magnesium-titanium-based composition. However, if the magnesium-titanium-based composition is to be partially activated with an organoaluminum compound before it is introduced into the reactor, it should be partially activated before the titanium tetraalkoxide is impregnated over it.

Both the titanium tetraalkoxide and activator compound employed are conveniently and preferably sprayed into the reactor dissolved in an inert liquid solvent, i.e., a solvent which is nonreactive with all the components of the catalyst composition and all other active components of the reaction system. Hydrocarbons such as isopentane, hexane, heptane, toluene, xylene, naphtha and mineral oil are preferred for this purpose. Generally, the titanium tetraalkoxide solution employed contains from 0.1 weight percent to 75 weight percent of such compound, usually from 5 weight percent to 40 weight percent of such compound, while the solution containing the activator compound generally contains from 5 weight percent to 75 weight percent of such compound. If desired, less concentrated or more concentrated solutions can be employed, or, alternatively, the titanium tetraalkoxide and activator compound can be added in the absence of solvent.

Any solvent employed to introduce the titanium tetraalkoxide and activator compound into the reactor is, of course, immediately vaporized in the reactor so that gaseous conditions are maintained in the reactor at all times. The amount of solvent employed should, of course, be carefully controlled so as to avoid the use of excessive quantities of liquid which would prevent the rapid vaporization thereof.

The activator compound is added to the reactor in such amounts as to provide a total aluminum:titanium atomic ratio of from about 5:1 to about 500:1. While high ratios result in good copolymer production rates, such ratios also cause significant deactivation of the dimerization catalyst as well as a high degree of ethylene hydrogeneration. For this reason, it is preferred to maintain an aluminum:titanium atomic ratio of from about 5:1 to about 150:1.

The amount of titanium tetraalkoxide employed in the process depends upon the amount of butene-1 desired for copolymerization with ethylene. The greater the amount of butene-1 desired for copolymerization with ethylene, the greater the amount of titanium tetraalkoxide that must be employed. By the addition of progressively larger amounts of titanium tetraalkoxide to the reactor, copolymers having progressively lower densities are obtained at any given melt index. However, since the polymerization activity of the magnesium-titanium-based catalyst component decreases as the concentration of titanium tetraalkoxide increases, excessive amounts of titanium tetraalkoxide should be avoided. Of course, if desired, in order to avoid this problem, or for any other reason, it is possible to add butene to the reactor from an external source rather than generating it completely in situ. If desired, this butene may be produced by the dimerization of ethylene employing the dimerization catalyst and procedure described herein, but in the absence of the ethylene polymerization catalyst. Although the dimerization reaction and polymerization reaction proceed side by side in the presence of both the dimerization catalyst and the polymerization catalyst, the two reactions are entirely independent of each other, and each is capable of proceeding independently of the other in the absence of the catalyst for the complementary reaction. Hence, it is possible to independently dimerize ethylene outside the reactor using only a dimerization catalyst and employ the dimerized product together with dimer generated in situ in the reactor in the presence of both the dimerization catalyst and the polymerization catalyst. As long as the total concentration of butene in the reactor remains constant, the copolymer product is not influenced by the source of the butene. The reaction conditions employed for the dimerization of ethylene in the absence of the ethylene polymerization catalyst are the same as those employed in its presence, except that in the absence of the polymerization catalyst, the activator compound may be employed in a somewhat lesser amount, e.g., in an amount which will provide an aluminum:titanium ratio of as little as about 4:1.

Generally the titanium tetraalkoxide is employed in the process in an amount which will provide an atomic ratio of titanium in the titanium tetraalkoxide to titanium in the magnesium-titanium-based composition of from about 0.01:1 to about 50:1. In order to produce copolymers having a density of greater than about 0.94 g/cm$^3$ up to about 0.96 g/cm$^3$, a ratio of from about 0.01:1 up to about 2:1 is normally required. Ratios of greater than about 2:1 to about 20:1 usually result in copolymers having a density of from about 0.91 g/cm$^3$ up to about 0.94 g/cm$^3$. Densities of less than about 0.91 g/cm$^3$ generally require a ratio greater than about 20:1 up to about 50:1 for densities as low as about 0.86 g/cm$^3$. In order to produce copolymers having a density of less than about 0.91 g/cm$^3$, however, it is necessary to follow the precautions set forth in European patent publication 0 120 503, by Frederick John Karol et al., entitled "Preparation Of Low Density, Low Modulus Ethylene Copolymers In A Fluidized Bed", the disclosure of which is incorporated herein by reference.

The simultaneous dimerization of ethylene and copolymerization of ethylene with the dimerized product is effected, according to the present invention, in a continuous, fluidized bed process by continuously contacting ethylene gas with a catalytically effective amount of the catalyst system of the present invention in a fluidized bed reactor. In accordance with the process, discrete portions of the catalyst components are continually fed to the reactor together with ethylene gas while polymer product is continually removed during the continuing process. Fluid bed reactors suitable for continuously preparing ethylene copolymers have been previously described and are well known in the art. Fluid bed reactors useful for this purpose are described, e.g., in U.S. Pat. Nos. 4,302,565, 4,302,566 and 4,303,771, the disclosures of which are incorporated herein by reference.

If desired, the ethylene gas feed may be diluted with an inert gas, i.e., a gas which is nonreactive with all the components of the catalyst composition and all other active components of the reaction system. The gaseous reaction mixture should, of course, be substantially free of catalyst poisons, such as moisture, oxygen, carbon monoxide, carbon dioxide, acetylene and the like.

Hydrogen may also be added to the reaction mixture as a chain transfer agent to regulate molecular weight. Generally, hydrogen is added to the reaction mixture in an amount sufficient to produce a hydrogen:ethylene mol ratio of from about 0.01:1 to about 5:1. In addition to hydrogen, other chain transfer agents may be employed to regulate the molecular weight of the copolymers.

The simultaneous dimerization of ethylene and copolymerization of ethylene with the dimerized product is readily effected at a temperature of from about 30° C. to about 115° C. The temperature employed, of course, must be maintained below the sintering temperature of the copolymers produced in order to prevent polymer agglomerization. When copolymers having a density of from 0.91 g/cm$^3$ to 0.96 g/cm$^3$ are desired, temperatures of from about 75° C. to about 115° C., preferably from about 75° C. to about 100° C., are usually employed. When producing copolymers having a density of less than 0.91 g/cm$^3$, lower temperatures of from about 30° C. to about 80° C., preferably from about 40° C. to about 60° C., should be employed because of the lower sintering temperature of the product. In the latter case, it is also necessary to dilute the reaction mixture with a large quantity of a diluent gas to help prevent agglomeration and sustain polymerization on a continuous basis, as described in European patent publication No. 0 120 503, by Frederick John Karol et al, supra.

Pressures of up to about 7000 kPa can be employed in the process, although pressures of from about 70 kPa to about 2500 kPa are preferred. The ethylene partial pressure is preferably maintained between about 56 kPa to about 1900 kPa.

In order to maintain a viable fluidized bed, the superficial gas velocity of the gaseous reaction mixture through the bed must exceed the minimum flow required for fluidization, and preferably is at least 0.06 meter per second above the minimum flow. Ordinarily the superficial gas velocity does not exceed 1.5 meters per second, and most usually no more than 0.75 meters per second is sufficient.

The copolymers produced in accordance with the process of the present invention usually have a density of from 0.86 g/cm$^3$ to 0.96 g/cm$^3$. Such copolymers contain from about 50 mol percent to about 99 mol percent of polymerized ethylene, and from about 1 mol percent to about 50 mol percent of polymerized butene-1.

The ethylene copolymers produced in accordance with the process of the present invention have a standard or normal load melt index of from 0 g/10 minutes to about 100 g/10 minutes, preferably of from about 0.2 g/10 minutes to about 80 g/10 minutes. Such polymers have a high load melt index (HLMI) of from greater than 0 g/10 minutes to about 2500 g/10 minutes. The melt index of a polymer varies inversely with its molecular weight and is a function of the polymerization temperature of the reaction, the density of the polymer, and the hydrogen/ethylene ratio in the reaction system. Thus, the melt index is raised by increasing the polymerization temperature and/or by increasing the hydrogen/ethylene ratio.

The ethylene copolymers produced in accordance with the process of the present invention have a melt flow ratio (MFR) of from about 22 to about 40, preferably of from about 25 to about 35. Melt flow ratio is anther means of indicating the molecular weight distribution ($M_w/M_n$ of a polymer. An MFR in the range of from about 22 to about 40 corresponds to a $M_w/M_n$ of from about 2.7 to about 6.5, and an MFR in the range of from about 25 to about 35 corresponds to a $M_w/M_n$ of from about 2.8 to about 4.8.

The ethylene copolymers produced in accordance with the process of the present invention are granular materials having an average particle size of from about 0.02 to about 0.20 centimeters, usually of from about 0.05 to about 0.13 centimeters, in diameter. The particle size is important for the purpose of readily fluidizing the polymer particles in the fluid bed reactor. These granular materials also contain no more than 4.0 percent of fine particles having a diameter of less than 0.005 inches.

The ethylene polymers produced in accordance with the process of the present invention have a bulk density of from about 240 kilograms per cubic meter to about 513 kilograms per cubic meter.

The following Examples are designed to illustrate the process of the present invention and are not intended as a limitation upon the scope thereof.

The properties of the polymers produced in the Examples was determined by the following test methods:

Density

ASTM D-1505 procedure is followed for polymers having a density of less than 0.940 g/cm$^3$, and a modified procedure is used for polymers having a density of 0.940 g/cm$^3$ or more. For the low density polymers, a plaque is made and conditioned for one hour at 100° C. to approach equilibrium crystallinity. For the high density polymers, the plaque is conditioned for one hour at 120° C. to approach equilibrium crystallinity, and is then quickly cooled to room temperature. Measurement for density is then made in a density gradient column and density values are reported as grams/cm$^3$.

Melt Index (MI)

ASTM D-1238, Condition E. Measured at 190° C. and reported as grams per 10 minutes.

Flow Index (HLMI)

ASTM D-1238, Condition F. Measured at 10 times the weight used in the melt index test above.

Melt Flow Ratio (MFR)

Ratio of Flow Index:Melt Index

Productivity

A sample of the resin product is ashed, and the weight percent of ash is determined. Since the ash is essentially composed of the catalyst, the productivity is thus the kilograms of polymer produced per kilogram of total catalyst consumed.

Bulk Density

ASTM D-1895, Method B. The resin is poured via $\frac{3}{8}''$ diameter funnel into a 400 ml graduated cylinder to the 400 ml line without shaking the cylinder, and weighed by difference.

Average Particle Size

Calculated from sieve analysis data measured according to ASTM D-1921, Method A, using a 500 g sample. Calculations are based on weight fractions retained on the screen.

EXAMPLE 1

Impregnation of Support with Mg-Ti-Based Composition

In a 12 liter Flask equipped with a mechanical stirrer were placed 41.8 g (0.439 mol) of anhydrous MgCl$_2$ and 2.5 liters of tetrahydrofuran (THF). To this mixture, 29.0 g (0.146 mol) of TiCl$_3$·0.33 AlCl$_3$ were added over a $\frac{1}{2}$ hour period. The mixture was then heated at 60° C. for another $\frac{1}{2}$ hour in order to completely dissolve the material.

Five hundred grams (500 g) of silica was dehydrated by heating at a temperature of 600° C. and slurried in 3 liters of isopentane. The slurry was stirred while 186 ml. of a 20 percent by weight solution of triethylaluminum in hexane was added thereto over a $\frac{1}{4}$ period. The resulting mixture was then under a nitrogen purge at 60° C. over a period of about 4 hours to provide a dry, free-flowing powder containing 5.5 percent by weight of the aluminum alkyl.

The treated silica was then added to the solution prepared as above. The resulting slurry was stirred for ¼ and then dried under a nitrogen purge at a period of about 4 hours to provide a dry, impregnated, free-flowing powder.

EXAMPLE 2

Partial Activation of Mg-Ti-Based Composition (a) The silica-impregnated magnesium-titanium-based composition prepared in accordance with Example 1 was slurried in 3 liters of anhydrous isopentane and stirred while a 20 percent by weight solution of tri-n-hexylaluminum in anhydrous hexane was added thereto over a ¼ hour period. The tri-n-hexylaluminum solution as employed in an amount sufficient to provide 0.2 mols of this compound per mol of tetrahydrofuran in the magnesium-titanium-based composition. After addition of the tri-n-hexylaluminum was completed, stirring was continued for an additional ¼ hour. The mixture was then dried under a nitrogen purge at a temperature of 65±10° C. over a period of about 4 hours to provide a dry, free-flowing powder. This material was stored under dry nitrogen until it was needed.

(b) The procedure was repeated employing the tri-n-hexylaluminum solution in an amount sufficient to provide 0.6 mols of this compound per mol of tetrahydrofuran in the magnesium-titanium-based composition.

(c) The silica-impregnated magnesium-titanium-based composition prepared in accordance with Example 1 was partially activated with diethylaluminum chloride and tri-n-hexylaluminum employing the same procedure as in 2(b) except that a 20 percent by weight solution of diethylaluminum chloride in anhydrous hexane was added to the silica-impregnated magnesium-titanium-based composition slurry prior to the addition of the tri-n-hexylaluminum solution. The diethylaluminum chloride solution was added over a ¼ hour period in an amount sufficient to provide 0.4 mols of this compound per mol of tetrahydrofuran in the magnesium-titanium-based composition.

EXAMPLES 3 to 9

Ethylene was simultaneously dimerized to produce butene-1 and copolymerized with the dimerized product under varying reaction conditions in a fluid bed reactor system similar to that described and illustrated in U.S. Pat. Nos. 4,302,565, 4,302,566 and 4,303,771.

In each polymerization, silica-impregnated magnesium-titanium-based composition prepared in accordance with Example 1 and partially activated in accordance with Example 2(a) was continually fed to the polymerization reactor along with titanium tetraalkoxide, as a solution in isopentane, and trialkylaluminum, also as a solution in isopentane. The magnesium-titanium-based composition had the empirical formula $$Mg_3TiCl_{10}(THF)_8$$

wherein THF stands for tetrahydrofuran.

The ethylene gas employed, in each instance, was diluted with nitrogen, and hydrogen was added to the gaseous reaction mixture as a chain transfer agent to regulate the molecular weight of the copolymer produced. In examples 3 to 7, the butene was generated completely in situ by the dimerization of ethylene. In examples 8 and 9, additional butene was added to the gaseous reaction mixture in order to supplement that generated in the reactor.

Table 1 below sets forth the details of these polymerizations, as well as the properties of the polymers produced by such polymerizations and the productivity of each catalyst system.

Comparative Examples A and B

For comparative purposes, ethylene was homopolymerized in the absence of the titanium tetraalkoxide dimerization catalyst. Also for purposes of comparison, ethylene was copolymerized with butene-1 in the absence of the titanium tetraalkoxide dimerization catalyst using butene-1 which was provided completely from a source external to the reactor. For the homopolymerization, silica impregnated magnesium-titanium-based composition prepared in accordance with Example 1 and partially activated in accordance with Example 2(b) was employed. For the copolymerization, silica-impregnated magnesium-titanium-based composition prepared in accordance with Example 1 and partially activated in accordance with Example 2(c) was employed. The details of these polymerizations are set forth in Table 1 below along with the details of Example 3 to 9.

TABLE 1

| Example | Comparative Example A | Comparative Example B | 3 | 4 | 5 | 6 | 7 | 8 | 9 |
|---|---|---|---|---|---|---|---|---|---|
| Partial Activation of Mg—Ti Polym. Cat. | | | | | | | | | |
| Partial Activator | $(C_6H_{13})_3Al$ | $(C_2H_5)_2AlCl/(C_6H_{13})_3Al$ | $(C_6H_{13})_3Al$ | $(C_6H_{13})_3Al$ | $(C_6H_{13})_3Al$ | $(C_6H_{13})_3Al$ | $(C_6H_{13})_3Al$ | $(C_6H_{13})_3Al$ | $(C_6H_{13})_3Al$ |
| Mol Ratio Partial Activator:Tetrahydrofuran | 0.6 | 0.4/0.6 | 0.2 | 0.2 | 0.2 | 0.2 | 0.2 | 0.2 | 0.2 |
| Reaction Conditions | | | | | | | | | |
| Mg—Ti Polym. Cat. Feed Rate, g/hr | 7 | 2 | 11 | 12 | 11 | 5 | 7 | 7 | 12 |
| Titanium Tetraalkoxide, [(RO)$_4$Ti] | None | None | (n-$C_4H_9O)_4Ti$ | (i-$C_4H_9O)_4Ti$ | (i-$C_4H_9O)_4Ti$ | (i-$C_4H_9O)_4Ti$ | (i-$C_4H_9O)_4Ti$ | (i-$C_4H_9O)_4Ti$ | (i-$C_4H_9O)_4Ti$ |
| Conc. (RO)$_4$Ti Soln., Wt. % | — | — | 1 | 5 | 5 | 5 | 5 | 5 | 5 |
| (RO)$_4$Ti Soln. Feed Rate, cc/hr | — | — | 200 | 20 | 85 | 69 | 62 | 80 | 44 |
| Conc. (RO)$_4$Ti in Fluid Bed, ppm | 0 | 0 | 40 | 60 | 85 | 110 | 130 | 100 | 60 |
| Activator (trialkylaluminum) | $(C_2H_5)_3Al$ | $(i-C_4H_9)_3Al$ | $(C_2H_5)_3Al$ | $(i-C_4H_9)_3Al$ | $(i-C_4H_9)_3Al$ | $(i-C_4H_9)_3Al$ | $(i-C_4H_9)_3Al$ | $(i-C_4H_9)_3Al$ | $(i-C_4H_9)_3Al$ |
| Conc. Activator Soln., Wt. % | 5 | 10 | 5 | 10 | 10 | 10 | 10 | 10 | 10 |
| Activator Soln. Feed Rate, cc/hr | 110 | 90 | 130 | 220 | 225 | 183 | 152 | 220 | 240 |
| Temperature, °C | 90 | 80 | 90 | 90 | 85 | 80 | 80 | 80 | 80 |
| Total Pressure, kPa | 2069 | 2069 | 2069 | 2069 | 2069 | 2069 | 2069 | 2069 | 2069 |
| Ethylene Partial Pressure, kPa | 897 | 690 | 862 | 828 | 897 | 855 | 690 | 552 | 552 |
| Nitrogen Partial Pressure, kPa | 616 | 848 | 578 | 827 | 437 | 487 | 813 | 1075 | 1087 |
| Hydrogen Partial Pressure, kPa | 556 | 179 | 603 | 290 | 188 | 171 | 159 | 110 | 99 |
| Butene/Ethylene Mol Ratio | — | 0.51 | 0.03 | 0.15 | 0.61 | 0.65 | 0.59 | 0.6 | 0.6 |
| Hydrogen/Ethylene Mol Ratio | 0.62 | 0.26 | 0.70 | 0.35 | 0.21 | 0.20 | 0.23 | 0.20 | 0.18 |
| Molar Ratio Al:Mg—Ti Polym. Cat. | 40 | 40 | 70 | 70 | 70–100 | 90 | 115 | 90 | 60 |
| Molar Ratio Al:(RO)$_4$Ti | — | — | 2–4 | 8–12 | 10–20 | 9 | 11 | 7–9 | 10–15 |
| Molar Ratio (RO)$_4$Ti:Mg—Ti Polym. Cat. | — | — | 1.3 | 5.5 | 10.5 | 14 | 8 | 10 | 4.5 |
| Polymer Properties | | | | | | | | | |
| Melt Index, g/10 Min. | 7.4 | 1.1 | 9.5 | 2.9 | 1.5 | 0.8 | 1.1 | 0.7 | 0.9 |
| Flow Index, g/10 Min. | 178.0 | 22.4 | 256.0 | 70.0 | 48.0 | 23.4 | 29.2 | 18.9 | 22.5 |
| Melt Flow Ratio | 24 | 21 | 27 | 24 | 32 | 29 | 27 | 27 | 25 |
| Density, g/cm$^3$ | 0.965 | 0.918 | 0.960 | 0.938 | 0.926 | 0.920 | 0.920 | 0.921 | 0.910 |
| Bulk Density, kg/m$^3$ | 368 | 417 | 401 | 352 | 352 | 336 | 336 | 384 | 256 |
| Average Particle Size, cm. | 0.08 | 0.08 | 0.05 | 0.08 | 0.08 | 0.10 | 0.08 | 0.10 | 0.20 |
| Productivity | | | | | | | | | |
| Ash, Wt. % | 0.035 | 0.035 | 0.039 | 0.059 | 0.064 | 0.055 | 0.059 | — | — |
| Kg Polymer/Kg Ash | 2857 | 2857 | 2564 | 1695 | 1563 | 1818 | 1695 | — | — |

EXAMPLE 10

Ethylene was simultaneously dimerized to produce butene-1 and copolymerized with the dimerized product in a large fluid bed reactor.

Silica-impregnated magnesium-titanium-based composition prepared in accordance with Example 1 and partially activated in accordance with Example 2(a) was continually fed to the polymerization reactor along with titanium tetraisobutoxide, as a solution in isopentane, and trisobutyaluminum, also as a solution in isopentane. The magnesium-titanium-based composition had the empirical formula $$Mg_3TiCl_{10}(THF)_8$$

wherein THF stands for tetrahydrofuran.

The ethylene gas employed was diluted with nitrogen, and hydrogen was added to the gaseous reaction mixture as a chain transfer agent to regulate the molecular weight of the copolymer produced.

Table 2 below sets forth the details of the polymerization, as well as the properties of the polymer produced and the productivity of the catalyst system.

TABLE 2

| Example | 10 |
|---|---|
| Partial Activation of Mg—Ti Polym. Cat. | |
| Partial Activator | $(C_6H_{13})_3Al$ |
| Mol Ratio Partial Activator:Tetrahydrofuran | 0.2 |
| Reaction Conditions | |
| Mg—Ti Polym. Cat. Feed Rate, g/hr | 318 |
| Titanium Tetraalkoxide, [(RO)$_4$Ti] | $(i-C_4H_9O)_4Ti$ |
| Conc.(RO)$_4$Ti Solution, Wt. % | 5 |
| (RO)$_4$Ti Solution Feed Rate, l/hr | 6.4 |
| Conc.(RO)$_4$Ti in Fluid Bed, ppm | 56 |
| Activator | $(i-C_4H_9)_3Al$ |
| Conc. Activator Solution, Wt. % | 20 |
| Activator Soln. Feed Rate, l/hr | 16.5 |
| Temperature, °C. | 80 |
| Total Pressure, kPa | 1862 |
| Ethylene Partial Pressure, kPa | 759–828 |
| Nitrogen Partial Pressure, kPa | 473 |
| Hydrogen Partial Pressure, kPa | 198 |
| Gas Velocity, m/sec | 0.55 |
| Space Time Yield, kg/hr/m$^3$ | 80 |
| Butene/Ethylene Mol Ratio | 0.5 |
| Hydrogen/Ethylene Mol Ratio | 0.25 |
| Molar Ratio Al:Mg—Ti Polym. Cat. | 77 |
| Molar Ratio Al:(RO)$_4$Ti | 18 |
| Molar Ratio (RO)$_4$Ti:Mg—Ti Polym Cat. | 4.3 |
| Polymer Properties | |
| Melt Index, g/10 Min. | 1.0 |
| Flow Index, g/10 Min. | 26 |
| Melt Flow Ratio | 26 |
| Density, g/cm$^3$ | 0.919 |
| Bulk Density, kg/m$^3$ | 336–352 |
| Average Particle Size, cm. | 0.10 |
| Productivity | |
| Ash, Wt. % | 0.028 |
| Kg Polymer/Kg Ash | 3571 |

Gas analysis showed that butene-1 was generated by the dimerization at a selectivity in excess of 85 percent. Among the butene isomers produced, butene-1 was produced at a selectivity in excess of 93 percent.

We claim:

1. A continuous process for simultaneously dimerizing ethylene to produce butene-1 and copolymerizing ethylene with the dimerized product in a fluidized bed which comprises continuously contacting ethylene in a fluid bed reactor, at a temperature of from 30° C. up to 115° C. and a pressure no greater than 7000 kPa, with a catalytically effective amount of a catalyst system comprising:

(a) a titanium tetraalkoxide having the formula $$Ti(OR)_4$$

wherein each R is a hydrocarbon radical free from aliphatic unsaturation containing from 1 to 12 carbon atoms, (b) a magnesium-titanium-based composition having the formula $$Mg_mTi(OR')_nX_p[ED]_q$$

wherein

R' is an aliphatic or aromatic hydrocarbon radical containing from 1 to 14 carbon atoms, or COR" wherein R" is an aliphatic or aromatic hydrocarbon radical containing from 1 to 14 carbon atoms.

X is selected from the group consisting of Cl, Br, I, and mixtures thereof,

ED is an organic electron donor compound selected from the group consisting of alkyl esters of aliphatic and aromatic carboxylic acids, aliphatic ethers, cyclic ethers and aliphatic ketones, m is 0.5 to 56, n is 0, 1 or 2, p is 2 to 116, and q is 2 to 85 said magnesium-titanium-based composition being diluted with an inert carrier material, and (c) a trialkylaluminum compound having the formula $$AlR_3'''$$

wherein each R''' is a saturated hydrocarbon radical containing from 1 to 14 carbon atoms, said titanium tetraalkoxide and said magnesium-titanium-based composition being employed in such amounts as to provide an atomic ratio of titanium in the titanium tetraalkoxide to titanium in the magnesium-titanium-based composition of from 0.01:1 to 50:1, and said trialkylaluminum compound being employed in an amount such as to provide a total aluminum:titanium atomic ratio of from 5:1 to 500:1.

2. A process as in claim 1 wherein said magnesium-titanium-based composition is mechanically mixed with the inert carrier material and the blended mixture contains from 3 percent by weight to 50 percent by weight of the magnesium-titanium-based composition.

3. A process as in claim 1 wherein the inert carrier material is impregnated with the magnesium-titanium-based composition and the impregnated carrier contains from 3 percent by weight to 50 percent by weight of the magnesium-titanium-based composition.

4. A process as in claim 3 wherein the inert carrier material is silica.

5. A process as in claim 4 wherein the magnesium-titanium-based composition is partially activated before it is introduced into the polymerization reactor by means of an organoaluminum activator compound, said activator compound being employed in an amount which does not raise the molar ratio of activator compound:electron donor in the magnesium-titanium-based composition beyond 1.4:1, and said activator compound having the formula $$Al(R''')_d X_{e'} H_f$$

wherein

X' is Cl or OR'''',

R''' and R'''' are saturated hydrocarbon radicals containing from 1 to 14 carbon atoms, e is 0 to 1.5, f is 0 or 1, and d+e +f=3.

6. A process as in claim 5 wherein R is an aliphatic radical containing from 1 to 6 carbon atoms, X is Cl, [ED] is tetrahyrdrofuran, m is 1.5 to 5, n is 0, p is 6 to 14, and q is 3 to 10.

7. A process as in claim 6 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

8. A process as in claim 5 wherein a portion of the butene-1 is added to the reactor from an external source.

9. A process as in claim 8 wherein R is an aliphatic radical containing from 1 to 6 carbon atoms, X is Cl, [ED] is tetrahydrofuran, m is 1.5 to 5, n is 0, p is 6 , and q is 3 to 10.

10. A process as in claim 9 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

11. A process as in claim 5 wherein the organoaluminum activator compound employed to partially activate the magnesium-titanium-based composition is employed in an amount which will provide the magnesium-titanium-based composition with an activator compound:electron donor molar ratio of from 0.1:1 to 1.0:1.

12. A process as in claim 11 wherein R is an aliphatic radical containing from 1 to 6 carbon atoms, X is Cl, [ED] is tetrahydrofuran, m is 1.5 to 5, n is 0, p is 6 to 14, and q is 3 to 10.

13. A process as in claim 12 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

14. A process as in claim 11 wherein a portion of the butene-1 is added to the reactor from an external source.

15. A process as in claim 14 wherein R is an aliphatic radical containing from 1 to 6 carbon atoms, X is Cl, [ED] is tetrahydrofuran, m is 1.5 to 5, n is 0, p is 6 to 14, and q is 3 to 10.

16. A process as in claim 15 wherein the titanium tetraalkoxide is titanium tetraiisobutoxide; the magnesium-titanium-based composition is composed of magnesium dichloride, titanium trichloride, and tetrahydrofuran; and the trialkylaluminum compound is triisobutylaluminum.

17. A process as in claim 5 wherein a temperature of from 75° C. to 115° C. is employed, the titanium tetraalkoxide and magnesium-titanium-based composition are employed in such amounts as to provide an atomic ratio of titanium in the titanium tetraalkoxide to titanium in the magnesium-titanium-based composition of greater than 2:1 to 20:1, and the trialkylaluminum compound is employed in an amount such as to provide a total aluminum:titanium atomic ratio of 5:1 to 150:1.

18. A process as in claim 17 wherein R is an aliphatic radical containing from 1 to 6 carbon atoms, X is Cl, [ED] is tetrahydrofuran, m is 1.5 to 5, n is 0, p is 6 to 14, and q is 3 to 10.

19. A process as in claim 18 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

20. A process as in claim 17 wherein a portion of the butene-1 is added to the reactor from an external source.

21. A process as in claim 20 wherein R is an aliphatic radical containing from 1 to 6 carbon atoms, X is Cl, [ED] is tetrahydrofuran, m is 1.5 to 5, n is 0, p is 6 to 14, and q is 3 to 10.

22. A process as in claim 21 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

23. A process as in claim 11 wherein a temperature of from 75° C. to 115° C. is employed, the titanium tetraalkoxide and magnesium-titanium-based composition are employed in such amounts as to provide an atomic ratio of titanium in the titanium tetraalkoxide to titanium in the magnesium-titanium-based composition of greater than 2:1 to 20:1, and the trialkylaluminum compound is employed in an amount such as to provide a total aluminum:titanium atomic ratio of 5:1 to 150:1.

24. A process as in claim 23 wherein R is an aliphatic radical containing from 1 to 6 carbon atoms, X is Cl, [ED] is tetrahydrofuran, m is 1.5 to 5, n is 0, p is 6 to 14, and q is 3 to 10.

25. A process as in claim 24 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

26. A process as in claim 23 wherein a portion of the butene-1 is added to the reactor from an external source.

27. A process as in claim 26 wherein R is an aliphatic radical containing from 1 to 6 carbon atoms, X is Cl, [ED] is tetrahydrofuran, m is 1.5 to 5, n is 0, p is 6 to 14, and q is 3 to 10.

28. A process as in claim 27 wherein the titanium tetraalkoxide is titanium tetraisobutoxide; the magnesium-titanium-based composition is composed of magnesium dichloride, titanium trichloride, and tetrahydrofuran; and the trialkylaluminium compound is triisobutylaluminum.

29. A process as in claim 3 wherein the ethylene feed is diluted with an inert gas, the ethylene partial pressure is between 56 kPa and 1900 kPa, and hydrogen is added to the reaction mixture in an amount sufficient to produce a hydrogen:ethylene molar ratio of from 0.01:1 to 5:1.

30. A process as in claim 29 wherein the inert carrier material is silica.

31. A process as in claim 30 wherein the magnesium-titanium-based composition is partially activated before it is introduced into the polymerization reactor by means of an organoaluminum activator compound, said activator compound being employed in an amount which does not raise the molar ratio of activator compound:electron donor in the magnesium-titanium-based composition beyond 1.4:1, and said activator compound having the formula

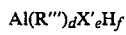

wherein
X' is Cl or OR'''',
R''' and R'''' are saturated hydrocarbon radicals containing from 1 to 14 carbon atoms,
e is 0 to 1.5,
f is 0 or 1, and
d+e+f=3.

32. A process as in claim 31 wherein R is an aliphatic radical containing from 1 to 6 carbon atoms, X is Cl, [ED] is tetrahydrofuran, m is 1.5 to 5, n is 0, p is 6 to 14, and q is 3 to 10.

33. A process as in claim 32 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

34. A process as in claim 31 wherein a portion of the butene-1 is added to the reactor from an external source.

35. A process as in claim 34 wherein R is an aliphatic radical containing from 1 to 6 carbon atoms, X is Cl, [ED] is tetrahydrofuran, m is 1.5 to 5, n is 0, p is 6 to 14, and q is 3 to 10.

36. A process as in claim 35 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

37. A process as in claim 31 wherein the organoaluminum activator compound employed to partially activate the magnesium-titanium-based composition is employed in an amount which will provide the magnesium-titanium-based composition with an activator compound:electron donor molar ratio of from 0.1:1 to 1.0:1.

38. A process as in claim 37 wherein R is an aliphatic radical containing from 1 to 6 carbon atoms, X is Cl, is tetrahydrofuran, m is 1.5 to 5, n is 0, p is 6 to 14, and q is 3 to 10.

39. A process as in claim 38 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

40. A process as in claim 37 wherein a portion of the butene-1 is added to the reactor from an external source.

41. A process as in claim 40 wherein R is an aliphatic radical containing from 1 to 6 carbon atoms, X is Cl, [ED] is tetrahydrofuran, m is 1.5 to 5, n is 0, p is 6 to 14, and q is 3 to 10.

42. A process as in claim 41 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

43. A process as in claim 31 wherein a of from 75° C. to 115° C. is employed, the titanium tetraalkoxide and magnesium-titanium-based composition are employed in such amounts as to provide an atomic ratio of titanium in the titanium tetraalkoxide to titanium in the magnesium-titanium-based composition of greater than 2:1 to 20:1, and the trialkylaluminum compound is employed in an amount such as to provide a total aluminum:titanium atomic ratio of 5:1 to 150:1.

44. A process as in claim 43 wherein R is an aliphatic radical containing from 1 to 6 carbon atoms, X is Cl, [ED] is tetrahydrofuran, m is 1.5 to 5, n is 0, p is 6 to 14, and q is 3 to 10.

45. A process as in claim 44 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

46. A process as in claim 43 wherein a portion of the butene-1 is added to the reactor from an external source.

47. A process as in claim 46 wherein R is an aliphatic radical containing from 1 to 6 carbon atoms, X is Cl, [ED] is tetrahydrofuran, m is 1.5 to 5, n is 0, p is 6 to 14, and q is 3 to 10.

48. A Process as in claim 47 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

49. A process as in claim 37 wherein a temperature of from 75° C. to 115° C. is employed, the titanium tetraalkoxide and magnesium-titanium-based composition are employed in such amounts as to provide an atomic ratio of titanium in the titanium tetraalkoxide to titanium in the magnesium-titanium-based composition of greater than 2:1 to 20:1, and the trialkylaluminum compound is employed in an amount such as to provide a total aluminum:titanium atomic ratio of 5:1 to 150:1.

50. A process as in claim 49 wherein R is an aliphatic radical containing from 1 to 6 carbon atoms, X is Cl, [ED] is tetrahydrofuran, m is 1.5 to 5, n is 0, p is 6 to 14, and q is 3 to 10.

51. A process as in claim 50 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

52. A process as in claim 49 wherein a portion of the butene-1 is added to the reactor from an external source.

53. A process as in claim 52 wherein R is an aliphatic radical containing from 1 to 6 carbon atoms, X is Cl, [ED] tetrahydrofuran, m is 1.5 to 5, n is 0, p is 6 to 14, and q is 3 to 10.

54. A process as in claim 53 wherein the titanium tetraalkoxide is titanium tetraisobutoxide; the magnesium-titanium-based composition is composed of magnesium dichloride, titanium trichloride, and tetrahydrofuran; and the trialkylaluminum compound is triisobutylaluminum.

55. A continuous process for dimerizing ethylene to produce butene-1 in a fluidized bed which comprises continuously contacting ethylene in a fluid bed reactor, at a temperature of from 30° C. up to 115° C. and a pressure no greater than 7000 kPa, with a catalytically effective amount of a catalyst system comprising
(a) a titanium tetraalkoxide having the formula $$Ti(OR)_4$$

wherein each R is a hydrocarbon radical free from aliphatic unsaturation containing from 1 to 12 carbon atoms, and (b) a trialkylaluminum compound having the formula AlR$_3'''$ wherein each R''' is a saturated hydrocarbon radical containing from 1 to 14 carbon atoms, said trialkylaluminum compound being employed in an amount such as to provide a total aluminum:titanium atomic ratio of from 4:1 to 500:1.

56. A process as in claim 55 wherein R is an aliphatic radical containing from 1 to 6 carbon atoms.

57. A process as in claim 56 wherein the titanium tetraalkoxide is titanium tetraisobutoxide and the trialkylaluminum compound is triisobutylaluminum.

58. A process as in claim 55 wherein a temperature of from 75° C. to 115° C. is employed, and the trialkylaluminum compound is employed in an amount such as to provide a total aluminum:titanium atomic ratio of 5:1 to 150:1.

59. A process as in claim 58 wherein R is an aliphatic radical containing from 1 to 6 carbon atoms.

60. A process as in claim 59 wherein the titanium tetraalkoxide is titanium tetraisobutoxide and the trialkylaluminum compound is triisobutylaluminum.

* * * * *